United States Patent [19]

Mount, II

[11] Patent Number: 4,899,219

[45] Date of Patent: Feb. 6, 1990

[54] MACROVIEW AND MICROVIEW VIDEO RECORD OF CORE

[75] Inventor: Houston B. Mount, II, Tulsa, Okla.

[73] Assignee: Amoco Corporation, Chicago, Ill.

[21] Appl. No.: 265,089

[22] Filed: Oct. 31, 1988

[51] Int. Cl.⁴ .............................................. H04N 7/18
[52] U.S. Cl. .................................... 358/107; 358/101; 73/153
[58] Field of Search .................. 73/153; 358/101, 107, 358/106, 93, 102; 250/255

[56] References Cited

U.S. PATENT DOCUMENTS

| | | | |
|---|---|---|---|
| 3,373,440 | 3/1968 | Jenkins et al. | 73/153 |
| 4,589,140 | 5/1986 | Bishop et al. | 358/106 |
| 4,692,943 | 9/1987 | Pietzsch et al. | 358/107 |
| 4,710,946 | 12/1987 | Hinch et al. | 250/255 |
| 4,764,969 | 8/1988 | Ohtomabe et al. | 358/107 |

OTHER PUBLICATIONS

"Continuous Wireless Core Drilling: An Alternative Method for Oil and Gas Exploration"; R. E. Swayne; Drill Bits; pp. 7-12; Spring 1988 (no dates).

*Primary Examiner*—John K. Peng

[57] ABSTRACT

A macroscopic and microscopic video record of whole core is stored by translating the core in increments adjacent a video recording station. The core is stopped and movement damped prior to storing the video record for each increment. Overlapping or contiguous macroviews are made using a video camera and in the center of each macroview a microview is also video recorded. The video records are stored in a random access video memory and are retrievable by depth. Macro and microviews of any depth can be instantaneously retrieved and viewed and scanning up or down by depth is also possible.

19 Claims, 1 Drawing Sheet

MACROVIEW AND MICROVIEW VIDEO RECORD OF CORE

FIELD OF THE INVENTION

The invention relates to the exploration for oil and gas by taking and analyzing full barrel core. In a particular aspect, the invention relates to method and apparatus for providing a video record of such core for analysis and archival purposes.

SETTING OF THE INVENTION

U.S. Pat. No. 3,373,440 describes customary practice in the drilling of some oil and gas wells. When the drilling bit approaches a formation which may contain oil and gas, a coring bit and core barrel are substituted for a drill bit and core samples are taken. The core samples can then be analyzed for such characteristics as lithology, porosity, permeability, oil and water saturation, and the like. Such analysis typically occurs in a commercial laboratory, which provides such services to the industry. U.S. Pat. No. 3,373,440, particularly, relates to a system for photographing cores and detecting radiation from core.

More recently, it is proposed to drill stratigraphic exploration wells using special coring bits and core barrels and to take core along substantially the entire depth of penetration. The core is then analyzed for indicia of the presence of oil and gas.

Compared to the previous practice of coring only portions of a well, the practice of stratigraphic exploration requires thousands of feet of full barrel core to be produced from each well. The produced core must then be preliminarily analyzed, at least sufficiently to show which portions of the core should be subjected to a more detailed analysis and to provide information in correlating data from the well with information obtained from logging, aeromagnetic surveys, seismic exploration, and the like.

Preserved images of the core are useful for later analysis and comparison and for archival purposes in connection with stratigraphic exploration wells. However, such a photography technique as described in U.S. Pat. No. 3,373,440, if applied to continuous coring of substantially the entire depth of penetration of a wellbore would require handling of the prints, provides only a macroscopic view, and presents handling inconvenience when a particular depth interval of the well is desired to be examined or compared with another interval of the well or of another well.

Further, in many circumstances, the geological analyst has reason to examine texture, grain size, and other microscopic aspects of cores. For such determinations, a magnified view, as through a microscope, can provide significant information, particularly where field dimensions are known.

Further, the geologist frequently desires to correlate such microscopic views with macroscopic structure such as bedding planes and the like, and to correlate different macroscopic structures with one another, for example, in the same or in different wells. For such applications, the systems described in U.S. Pat. No. 3,373,440 is not well suited.

Further, it is desirable to produce a color record of whole fresh core, i.e., core under substantially in situ conditions, since colors and subterranean structure, especially in shaly or rubbly zones are rapidly lost.

SUMMARY OF THE INVENTION

The invention comprises method and apparatus for providing a video record of whole core. Core supported by a core trough is translated in increments to a video recording zone. For each increment of core, the movement of the core is stopped, vibration or jitter of the core resulting from movement are damped, and a video record of the increment of core is taken, annotated for retrieval, and stored in a random access video memory.

According to further aspects of the invention, the increments of core are selected to provide a continuous record of core; the video recording zone comprises a macroscopic view video recording station for recording a macroview of each increment of the core and a microscopic view video recording station for recording a microview in the field of each macroview; the macroview and microview are taken at separate but adjacent video recording stations; translation of the core is sensed and recorded by depth; both macro and microviews are quickly retrievable by depth without scanning the wellbore sequentially by depth; and the video record is made in the field on core under substantially in situ conditions to preserve a record of transient natural color and subterranean structure.

The invention will be further understood and appreciated from the following description and from FIG. 1, which illustrates method and apparatus in accordance with the invention.

DETAILED DESCRIPTION OF THE INVENTION

Figure 1:
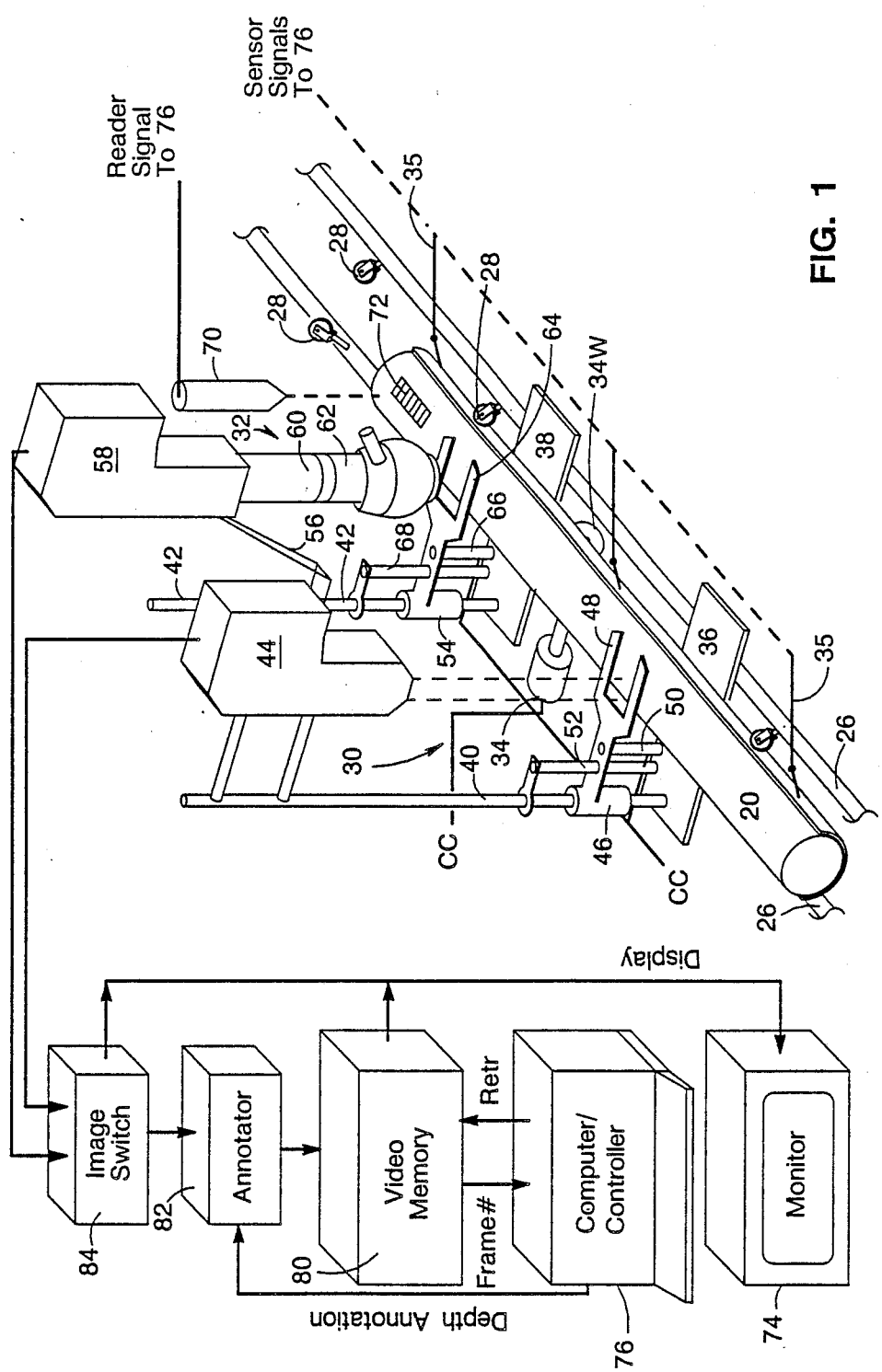

Referring now to FIG. 1, FIG. 1 illustrates method and apparatus in accordance with the invention. As shown in FIG. 1, full barrel core 20 supported, for example, by a semicylindrical core trough 24 is moved by motor 34 having friction drive wheel 34W, responsive to computer/controller 76, past a video station with video, preferably color video, cameras 44 and 58. The core trough is supported by rollers 28 on frame 26 during movement. The core is preferably washed to remove muds and surface particles.

Core 20 can have a bar code 72 or other indicia of depth affixed thereto to be sensed by a sensor such as bar code reader 70 which can provide the initial recorded depth of the section of core to computer/controller 76. Position sensors 35 positioned at spaced apart intervals along frame 26 to sense presence of the core and together with information relating to the rate of rotation of motor 34 can be used to provide a record of depth for each macro and microview as hereinafter described.

The video recording station can comprise two adjacent video recording stations 30 and 32. Recording station 30 is effective for producing a macroview of the core at increments along the core as it is translated and stopped incrementally adjacent the station. Microvideo recording station 32 is effective for producing a magnified view as through a microscope within the field of each macroview, as hereinafter described.

Referring now to the macrovideo station 30, the station can comprise support means adjacent translation means such as a baseplate 36 affixed to the frame 26 for supporting video camera 44. Video camera 44 can be positioned to take a video record of increments of the core as it is stopped beneath the video camera. Video station 30 can be further equipped with a clamp 48, slidably mounted by bearing mount 46 on railed support 40 for vertical up and down movement effected by pneumatic ram 50. Clamp 48 is preferably a two arm clamp defining a frame field of view for camera 44 between the arms of the clamp. Guide slide bar 52 can be provided parallel to railed support 40 to provide additional control for vertical movement of clamp 48. Ram 50 responds to a clamp signal from computer 76 for clamping core 20 following each increment of movement during the period when a video record from camera 44 is provided to video memory as below described. In addition to pneumatic ram 30 and motor 34, the video camera 44 may also be controlled by an activation signal from computer/controller 76; or alternatively as discussed below a selected video frame can be selected by switch 84 and provided to memory 80.

Microvideo recording station 32 likewise can comprise a baseplate 38 mounted to frame 26 to which a video camera railed support 42 is attached. Video camera 58 is slidably mounted by support frame 56 to railed support 42. Guide bar 68 is also provided. Clamp 64 is mounted by bearing mount 54 to railed guide 42 with guide bar 68 for vertical up and down movement effected by ram 66. Video camera 58 is provided with microscope adaptor 60 and microscope 62 focused so that when pneumatic ram 66 is actuated and clamp 64 clamps core 20 in place, the field of view of microscope 62 is focused at the plane of the bottom of the clamp 64 on the surface of the core.

It will be seen from FIG. 1 that at video station 32, clamp 64, camera 58, microscope 62, and ancillary structures are moved as a unit by ram 66.

During operation of the invented apparatus, core 20 is moved by motor 34 responsive to a motor control signal from computer/controller 76. Control is indicated by letters CC. As core 20 is moved adjacent sensor 70, the initial depth indication 72 is read and a signal provided to computer/controller 76 by sensor 70. As core 20 is moved in increments adjacent the position sensors 36, signals are provided to computer/controller 76 which uses information about the rate of rotation of motor 34 with friction drive 34W to provide a record of depth for each video record as it is being taken. The computer/controller 76 generates position signals for each view and provides position signals or depth signals to annotator 82 where it is used as described below.

Core 20 is preferably advanced in overlapping or contiguous field-of-view increments, for example, about 3 inches for a macroview for providing a complete record of core 20. For each field-of-view increment, each of pneumatic ram 50 and 66 is actuated clamping the core and damping vibrations induced in the core during the previous increment of movement. In the absence of such clamping, interlace jitter is observed in the horizontal field of even the macroview record of the core; and in the absence of clamping such interlace jitter and also blurring occurs in the microview record.

Interlace jitter results because odd and even lines of a standard video image are transmitted consecutively as separate fields which are superimposed to create one frame or complete picture at the receiver. Such separate fields occur at about 1/60 second rate. In the absence of damping it was observed that macroview frame resulting from the overlapping fields resulted in a zig zag effect in the image due to incompletely damped movement of the core even though the image was not blurred. In the absence of damping, both interlace jitter and blurring were observed in the microview frames. Clamps eliminated this problem and of course other methods of damping movement and vibration can also be used.

Clamping also facilitates rapid processing of core since vibrations may be rapidly damped, for example, in ½ second or less which would otherwise take several seconds to die away.

Upon clamping of the core at both of stations 32 and 30, image switch 84 under control of controller 76 provides a complete video frame from each of cameras 44 and 58 to annotator 82 and memory 80. Alternatively, the switch 84 can sequentially and continuously pass frames from each of cameras 44 and 58 and selected frames can be stored in video memory 80 upon command from controller 76. Each of cameras 44 and 58 generate video frames in a standard video format such as, for example, the standard American system of color telecasting referred to as NTSC (National Television System Committee) video. Preferably, switch 84 upon command receives from each video camera only a single frame, i.e., about 1/30 second (2 fields) and provides such to memory 80. Image switch 84 can sequentially switch between cameras 58 and 44 and receive a video frame from each and provide such video frame to annotator 82. Annotator 82 is effective for providing a depth indication on the NTSC frame record for each of the macroview and the microview. The depths will be different for the two records, but these can readily be maintained and separately updated by computer/controller 76.

Station 30 and station 32 are preferably spaced apart so that the microview of station 32 is centered in the field of the macroview of station 30 when corresponding depth intervals is adjacent thereto. Separate stations may also be used. The annotated frames of NTSC video macroview and microview are then provided from annotator 82 to a random access video memory 80 such as a laser disk. Memory 80 generates and provides a frame number for each stored video frame to computer/controller 76 which associates each frame number with the corresponding depth of the frame so that subsequently each frame can be retrieved by a depth command signal.

As a result, the macro and microvideo views can be randomly accessed by the analyst, i.e., substantially instantaneously accessed, by a depth display command signal corresponding to the depths desired to be viewed.

Video monitor 74 is provided for viewing the video frames as they are being produced to insure proper focus and for scanning the recorded video frames by depth under depth signal display command control from computer/controller 76 by the analyst. Continuous monitors (not illustrated) can also be used for cameras 44 and 58.

It will be appreciated that the invented method and apparatus are well suited to providing a continuous record of core, in both macro- and microviews, which can be substantially instantaneously retrieved from random access video memory for analysis by the geologist or archivist. By damping movement of the core at each station during making of the record, interlace jitter in the horizontal field of the video record and blurring are avoided and the speed of processing core is significantly improved. Each video frame of core is recorded with depth annotation thereon and such fields can be rapidly compared by the analyst from console control. The system is paperless, filmless, and provides also advantages of enabling the geologist to make qualitative and even roughly quantitative assessments of texture, grain size and other microscopic aspects of cores and to correlate such to macroscopic structure in the same or different wells.

It will also be appreciated that the invented method and apparatus are particularly useful for field application where a color video record of core can be made before transient color and structure are lost. Color of core is useful in interpreting subterranean lithology and stratigraphy and is rapidly lost as the core is exposed to drying and oxidizing conditions. Further, structure can also be irretrievably lost as the core ages particularly in shaly or rubbly zones. The method and apparatus of the invention provides a rugged, light, and compact system suitable for field use in preparing a continuous record of the surface of core under substantially in situ or fresh conditions.

While the invention has been described in terms of a preferred embodiment, the invention is not limited thereto but by the claims appended hereto interpreted in accordance with applicable principles of law.

What is claimed is:

1. Method for providing a video record of whole core comprising:
   translating whole core supported by a core trough in discrete increments to a video recording zone;
   for recording each increment of core, interrupting the movement of the core and dampening movement of the core and taking a video record of an increment of core in the video recording zone; and
   storing thus taken video records of increments of core in a random access video m emory for retrieval and display.

2. The Method of claim 1 wherein successive video records for successive increments of core are contiguous to provide a complete record of the surface of the core.

3. The method of claim 1 further comprising:
   providing core having color transients after removal from the subsurface; and
   providing a video record of such core prior to losing such transients.

4. The method of claim 1 further comprising:
   retrieving and displaying selected depths of the record substantially instantaneously from the random access video memory.

5. The Method of claim 1 wherein successive video records for successive increments of core overlap to provide a complete record of the surface of the core.

6. The Method of claim 1 further comprising:
   providing core having subterranean structure transients after removal from subsurface; and
   providing a video record of such core prior to losing such transients.

7. The Method of claim 1 wherein:
   the video recording zone comprises a macroscopic view video station for generating a macroview of each increment of the core, and a microscopic view video station for generating a microview in the field of each macroview, the macroview and microview video stations being separate but adjacent; and wherein:
   the method comprises generating for each increment of the core both a macroview and a microview.

8. The Method of claim 7 wherein each of the macroview and the microview are annotated by depth corresponding to each and stored in a random access video memory at a frame location retrievable by a command signal specifying a desired depth.

9. The Method of claim 7 wherein core is clamped during generating each of the macroview and microview effective to substantially prevent interlace jitter in the horizontal field of a resulting video record.

10. The Method of claim 7 wherein movement of core is damped during recording the macroview and microview thus bringing the core to a fixed recordable position in less time than in the absence of such damping.

11. The Method of claim 7 comprising:
   for each increment of core updating a depth identifier corresponding to each of the macroview and microview;
   sequentially receiving each of the macroview and microview and providing a single frame of NTSC video for each to an annotator for annotating each frame with its corresponding depth;
   storing each macroview and microview in the random access video memory and generating a frame identifier for each; and
   providing such frame identifier to a means for associating frame identifiers with corresponding depths and for retrieving the frames by control signals specifying depths.

12. The Method of claim 7 further comprising:
   displaying each frame as it is being generated.

13. Apparatus for providing a video record whole core comprising:
   video means for generating a video record of core in a video zone thereof;
   means for translating whole core supported by a core trough in discrete increments to the video zone of the video means;
   means for interrupting the movement of the core and dampening the vibrations of the core and for causing video means to generate video record of an increment of stopped core in the video zone; and
   means for storing the thus taken video records of increments of core in a random access video memory.

14. The Apparatus of claim 13 wherein:
   the video means comprises a macroscopic view video means for generating a macroview of each increment of the core and a microscopic view video means for generating a microview in the field of each macroview, the macroview and microview video means being separate and adjacent.

15. The Apparatus of claim 14 further comprising:
   means for annotating each of the macroview and the microview by depth corresponding to each and for storing the annotated views in the random access video memory at a location such that a frame at a depth is retrievable by a command signal specifying the depth.

16. The Apparatus of claim 14 further comprising:
   means for clamping core during generating and recording each of the macroview and microview effective to substantially prevent interlace jitter on the horizontal field of a resulting video record.

17. The Apparatus of claim 14 further comprising:
   means for clamping core during generating and recording each of the macroview and microview effective for bringing the core to a fixed recordable position without interleaf jitter or blurring in less time than in the absence of such clamping.

18. The Apparatus of claim 14 comprising:

depth updating means for updating a depth identifier corresponding to each of the macroview and microview for each increment of translation of core;

means for sequentially providing a single frame of NTSC video for each of the macroview and microview;

annotator means for receiving depth identifiers from the depth updating means and for annotating each frame with its corresponding depth;

the means for storing being effective for storing each annotated macroview and microview frame and for generating a frame identifier for each; and the means for storing further being effective for associating frame identifiers with corresponding depths for retrieving stored frames by control signals specifying depths.

19. The Apparatus of claim 14 further comprising:

means for displaying each frame as it is being generated.

* * * * *